United States Patent
Jarrell

(10) Patent No.: US 7,847,936 B2
(45) Date of Patent: Dec. 7, 2010

(54) EVAPORATIVE LIGHT SCATTERING DEVICE AND METHODS OF USE THEREOF

(75) Inventor: Joseph A. Jarrell, Newton Highlands, MA (US)

(73) Assignee: Waters Technologies Corporation, Milford, MA (US)

( * ) Notice: Subject to any disclaimer, the term of this patent is extended or adjusted under 35 U.S.C. 154(b) by 70 days.

(21) Appl. No.: 12/113,234

(22) Filed: May 1, 2008

(65) Prior Publication Data

US 2009/0122315 A1    May 14, 2009

Related U.S. Application Data

(60) Provisional application No. 60/938,017, filed on May 15, 2007.

(51) Int. Cl.
    *G01N 21/00* (2006.01)
(52) U.S. Cl. .................................................. 356/343
(58) Field of Classification Search .................. 356/343
    See application file for complete search history.

(56) References Cited

U.S. PATENT DOCUMENTS

| | | | |
|---|---|---|---|
| 3,398,286 A | | 8/1968 | Ford et al. |
| 3,624,835 A | * | 11/1971 | Wyatt ........................ 356/343 |
| 4,676,641 A | * | 6/1987 | Bott ........................... 356/336 |
| 4,761,074 A | | 8/1988 | Kohsaka et al. |
| 4,781,460 A | * | 11/1988 | Bott ........................... 356/336 |
| 4,794,086 A | | 12/1988 | Kasper et al. |
| 5,105,093 A | * | 4/1992 | Niwa .......................... 250/574 |
| 5,129,723 A | * | 7/1992 | Howie et al. ............... 356/336 |
| 5,164,787 A | * | 11/1992 | Igushi et al. ............... 356/336 |
| 5,185,641 A | * | 2/1993 | Igushi et al. ............... 356/336 |
| 5,374,396 A | | 12/1994 | Blackford et al. |
| 6,229,605 B1 | * | 5/2001 | Benedict ..................... 356/339 |
| 6,278,111 B1 | * | 8/2001 | Sheehan et al. ............. 250/288 |
| 6,421,121 B1 | * | 7/2002 | Haavig et al. ............... 356/338 |
| 6,568,245 B2 | | 5/2003 | Kaufman |
| 6,590,652 B2 | * | 7/2003 | Quist et al. .................. 356/338 |
| 6,639,672 B2 | * | 10/2003 | Haavig et al. ............... 356/338 |
| 6,774,994 B1 | * | 8/2004 | Wyatt et al. ................. 356/337 |

(Continued)

OTHER PUBLICATIONS

Anderson, et al; A Miniaturized Evaporative Light Scattering Detector For Application With Packed Microcolumn High-Performance Liquid Chromatography; J. Microcolumn Separations, 10(3) 249-254 (1998).

(Continued)

*Primary Examiner*—Roy Punnoose
(74) *Attorney, Agent, or Firm*—Anthony J. Janiuk; Siqun Huang

(57) ABSTRACT

Apparatus for the detection of analytes in a fluid, for example the eluant from a liquid chromatography is described. Solvent is evaporated from the eluant to produce a stream of particles when analyte is present in the fluid. The resultant stream of particles is passed through one or more beams of radiation, typically visible light, and radiation scattered by the particles is detected at least at a first angle to a beam of radiation and at a second, different, angle to a radiation beam to produce a signal indicative of the presence of the analyte.

Chromatographic apparatus incorporating the detector and methods of operating the detector and chromatographic apparatus are also described.

44 Claims, 5 Drawing Sheets

U.S. PATENT DOCUMENTS

| | | | |
|---|---|---|---|
| 6,778,271 | B2 | 8/2004 | Watson et al. |
| 7,057,724 | B1 * | 6/2006 | Mead et al. ................. 356/343 |
| 7,126,687 | B2 * | 10/2006 | Hill et al. .................... 356/336 |
| 2003/0086092 | A1 | 5/2003 | Gangloff et al. |
| 2005/0179904 | A1 * | 8/2005 | Larsen et al. ............... 356/446 |

OTHER PUBLICATIONS

Christie, William W.; Detectors for High-Performance Liquid Chromatography Of Lipids With Special Reference To Evaporative Light-Scattering Detection; Advances In Lipid Methodology, (1992) pp. 239-271.

Ford, Kennard; The evaporative analyser; Presented to the Seventh Australian Convention, Terrigal, New South Wales; (1966) pp. 299-313.

Koropchak, et al; Fundamental Aspects of Serosol-Based Light-Scattering Detectors for Separations; ch. 5 in Adv. In Chromatography, 2000 vol. 40 pp. 275-314 (Ed. Brown, Grushka).

Luzio, Gary A.; Use of an Evaporative Light Scattering Detector Coupled to MALLS for Determination of Polysaccharide Molecular Weights; Journal of Liquid Chromatography & Related Technologies, 2006 vol. 29 pp. 185-201.

Oppenheimer, Larry E.; Examination Of The Concentration Response Of Evaporative Light-Scattering Mass Detectors; Journal of Chromatography, 323 (1985) 297-304.

Righezza, Michel, et al; Effects Of The Nature Of The Solvent And Solutes On The Response Of A Light Scattering Detector; J. Liq. Chrom. 1988 vol. 11 (9, 10) pp. 1967-2004.

Scott, Raymond P.W.; Liquid Chromatography Detectors; Ch. "15 in Handbook of HPLC", Chromatogr. Sci. Ser. 1998 pp. 531-558 (Coden CHGSAL).

Mourey, et al; Principles of Operation of an Evaporative Light-Scattering Detector for Liquid Chromatography; Anal. Chem. 1984, 56, 2427-2434.

Waters Corp. Product Brochure, 2420 Evaporative Light Scattering Detector, No. 7200006 2 EN SH-FL, pub. 2003.

* cited by examiner

EVAPORATIVE LIGHT SCATTERING DEVICE AND METHODS OF USE THEREOF

CROSS REFERENCE TO RELATED APPLICATIONS

This application claims benefit of and is a continuation of U.S. Provisional Application No. 60/938,017, filed May 15, 2007 the content of which is incorporated herein by reference.

STATEMENT REGARDING FEDERAL SPONSORSHIP

The present invention was made without Federal Funds.

FIELD OF THE INVENTION

The invention relates to detectors that employ the scattering of light by analyte particles. The particles are produced by evaporation of solvent in which the compounds which comprise the particles are dissolved. Particular, embodiments of the invention comprise improved evaporative light scattering detectors for liquid of supercritical fluid chromatographs, and methods of operating them.

BACKGROUND OF THE INVENTION

As used herein, the term "Evaporative Light Scattering Detector" refers to an instrument comprising a nebulizer, a desolvation region, a light-scattering region, source of photons and a photo-detector for measuring the light scattered. ELSDs are capable of producing signals from a greater range of analytes than most other detectors, providing that the analytes are relatively involatile in comparison with the mobile phase in which the analytes are dissolved.

The term "sample" is used in the broadest sense to indicate something that one wishes to evaluate. Samples can originate with industrial materials, chemical synthesis, or may have originated from biological sources. The term "critical" refers to gases that are at critical temperature and pressure. The term supercritical refers to gases above such critical temperature or pressure. Gases will exhibit the solvation properties of a liquid at temperatures and pressure near the critical temperature and pressure. Supercritical fluids are used with cosolvents, or entrainers which modify, enhance or facilitate selection of a compound. This paper will refer to all such critical, near critical and supercritical fluids, and cosolvents and entrainers, as supercritical fluids unless the context of the text requires otherwise.

Chromatography is the science of separations based on differences in affinity that different compositions have to a stationary phase. High performance liquid chromatography (HPLC) is performed in columns or cartridges. Solutions in which samples are dissolved are pumped through the columns or cartridges. The columns and cartridges conduits have an inert stationary phase. The components of the sample separate as they move through the stationary phase due to the different affinity each compound has to the stationary phase. It desirable to detect the separated components with a detector. ELSDs are one form of detector that is used in chromatography.

This application will use the term HPLC as referring to separations at pressures up to approximately 3,000 pounds per square inch (psi). At higher pressures, it is possible to perform sharper better defined separations with greater speed. Higher pressures, referring now to the extreme high pressure range, approximately 4,000 psi to 15,000 psi, are now used. This paper will not distinguish between the high pressure range and the extreme pressure range and will use the term HPLC in reference to both unless the context requires otherwise.

The nebuliser of an ELSD is typically a pneumatic nebuliser. The nebuliser, when the ELSD is used with a chromatographic instrument, is disposed to receive the eluant from separation media and generate from it an aerosol that extends into the desolvation region. The desolvation region may comprise a heated drift tube wherein solvent is evaporated from the aerosol leaving a stream of particles. The particles then pass into the light scattering region where they pass through a light beam, typically disposed perpendicularly to the direction of travel of the particles, where they cause light to be scattered from the beam. A light detector is positioned to receive some of the scattered light and produces a signal indicative of the presence of the particles.

Unfortunately, prior types of ELSD sometimes lack the sensitivity of other types of detectors, and are often non-linear in their response to different quantities of a particular analyte, making quantitative use difficult.

SUMMARY OF EMBODIMENTS OF THE INVENTION

Embodiments of the present invention provide apparatus and methods for the detection of analytes present in a solution by the scattering of light by analyte-derived particles. Embodiments of the present invention have greater sensitivity and exhibit less variation with the quantity than prior apparatus and methods. Embodiments of the present invention are well suited for use with chromatographic instruments to detect analytes present in the eluant from a chromatographic separation medium.

One embodiment of the present invention features an apparatus for the detection of one or more analytes present in a fluid. The apparatus comprises vessel means in communication with a source of fluid. The vessel means is operable to evaporate solvent from said fluid and, in the presence of an analyte, to produce a stream of particles. The apparatus further comprises a radiation source in photo communication with said vessel means for generating at least one beam of radiation within the vessel means. The at least one beam of radiation is directed to and received by the stream of particles in the vessel means to produce at least one first reflected beam having a first scattering angle and to produce at least one second reflected beam having a second scattering angle. The apparatus further comprises radiation detection means in photo-communication with the vessel for receiving the first reflected beam at the first scattering angle and producing a first scattering angle signal and for receiving the second reflected beam at the second scattering angle and producing a second scattering angle signal. The first scattering angle signal and said second scattering angle signal are indicative of the presence or absence or quantity of an analyte.

As used herein, the term "stream" refers to the path taken by a majority of the particles. The term "beam" refers to the path of the radiation, for example, the path of photons. The term "photo-communication" refers to the ability to receive or transmit electro-magnetic radiation. The term "signal communication" refers to the ability to receive or transmit signals in the nature of exchanges of data over wires, optical lines or wireless transmission and receiving devices.

Preferably, the apparatus further comprising a source of fluid. The fluid is selected from the group of fluids comprising supercritical fluids and liquids. A preferred source is a chromatographic instrument. In such case the fluid is the eluant of the instrument.

Preferably, the radiation detection means comprises a first radiation detector and a second radiation detector. The first radiation detector is constructed and arranged to receive reflected radiation at the first scattering angle, and the second radiation detector is constructed and arranged to receive reflected radiation at the second scattering angle.

Preferably, the radiation source generates a first beam of radiation and a second beam of radiation. The radiation detection means is disposed to receive radiation reflected at the first scattering angle to the first beam of radiation and at the second scattering angle to the second beam of radiation. And, preferably, the radiation detection means comprises a first radiation detector and a second radiation detector. The first radiation detector is disposed to receive radiation scattered by the particles at the first angle to the first beam of radiation. And, the second radiation detector is disposed to receive radiation scattered by the particles at the second angle to the second beam of radiation.

Preferably, the radiation source generates at least one beam of radiation selected from the group comprising visible light, infrared radiation, and ultraviolet radiation.

Preferably, the radiation source is selected from the group comprising filament lamps, discharge lamps, arc lamps, light emitting diodes, laser diodes and lasers.

Preferably, the radiation detection means selected from the group comprising photomultipliers, photodiodes, phototransistors, other photosensitive solid state devices, scintillator devices and associated electron detectors, thermal detectors, and radiation sensitive film.

Preferably, the radiation source generates a first beam of radiation having a first frequency and a second beam of radiation having a second frequency, and wherein said first and second frequencies are different. This allows for separation of the signals derived from the different frequencies.

Preferably, the radiation beams and the radiation detection means are disposed in a plane substantially orthogonal to the stream of particles.

Preferably, the vessel means comprises a nebulizer and a heated drift region. The vessel means refers to any containment device including tanks, pipes and conduits through which fluid may enter, be desolvated and removed leaving particles.

Preferably, the radiation detection means comprises a plurality of radiation detectors and the radiation source for generating at least one beam of radiation comprises a plurality of radiation sources, such that the sum of the total number of radiation detectors and radiation sources is greater than four. For example, one embodiment of the present invention features two radiation sources and two radiation detectors. The radiation sources and the radiation detectors are, preferably, disposed so that between them they receive at least radiation scattered at a first angle to a first beam of radiation and at a second angle to the first or a second beam of radiation. The first angle and the second angles are selected to be different and, preferably, detected simultaneously.

Preferably, the apparatus further comprises signal processing means in signal communication with the radiation detection means. The signal processing means is for receiving the first scattering angle signal and the second scattering angle signal from the radiation detection means. As used herein, signal processing means refers to computer processing units (CPUs), computers, including mainframe, portable, personal, laptop, handheld, integral or separate, and analog circuitry.

Preferably, at least one of the first light scattering signal and the second light scattering signal has a frequency signature of the particles. And, the signal processing means comprises means for enhancing signals having the frequency signatures. These means for enhancing comprise isolation of the signals having the frequency signatures, amplification of the signals having frequency signatures, decreasing or minimizing signals that are not frequency signals and filters.

Preferably, the signal processing means comprises means for rejecting signals present for a time significantly longer than the transit time of the particles through at least one of the beams of radiation. And, preferably, the signal processing means associates signals characteristic of a particle passing through a said radiation beam received by said first radiation detector and said second radiation detectors at substantially the same time.

A further embodiment of the present invention is directed to a method of detecting the presence or absence of one or more analytes in a fluid. The method comprises the step of providing an apparatus as previous described and placing a fluid in the vessel means and forming a stream of particles. And, the method comprises the step of generating at least one beam of radiation directed at the stream of particles and receiving at least one reflected beam having a first scattering angle or a second scattering angle indicative of the presence or absence or quantity of an analyte.

Viewed from another aspect, an embodiment of the invention comprises a method of detecting the presence of one or more analytes in a fluid. The method comprises the step of evaporating solvent from the fluid to produce a stream of particles whenever the analyte is present in the fluid. The method further comprises the step of passing the stream of particles through one or more beams of radiation to produce scattering radiation. And, the method comprises the step of detecting such scattering radiation at a first angle to the beam of radiation and at a second, different, angle to the beam of radiation. The presence or absence or amount of scattering radiation is related to the composition and/or amount of the analyte.

Such a method may advantageously be employed for the detection of analytes in the eluant from liquid or supercritical fluid chromatographic separation media, for example as a method of detection for liquid or supercritical fluid chromatography. The radiation beam(s) of the method may advantageously comprise visible light, ultraviolet or infrared radiation.

These features and advantages, as well as others, will be readily recognized by individuals skilled in the art upon viewing the Figures and reading the detailed descriptions that follow.

DETAILED DESCRIPTION OF EMBODIMENTS OF THE INVENTION

Figure 1:
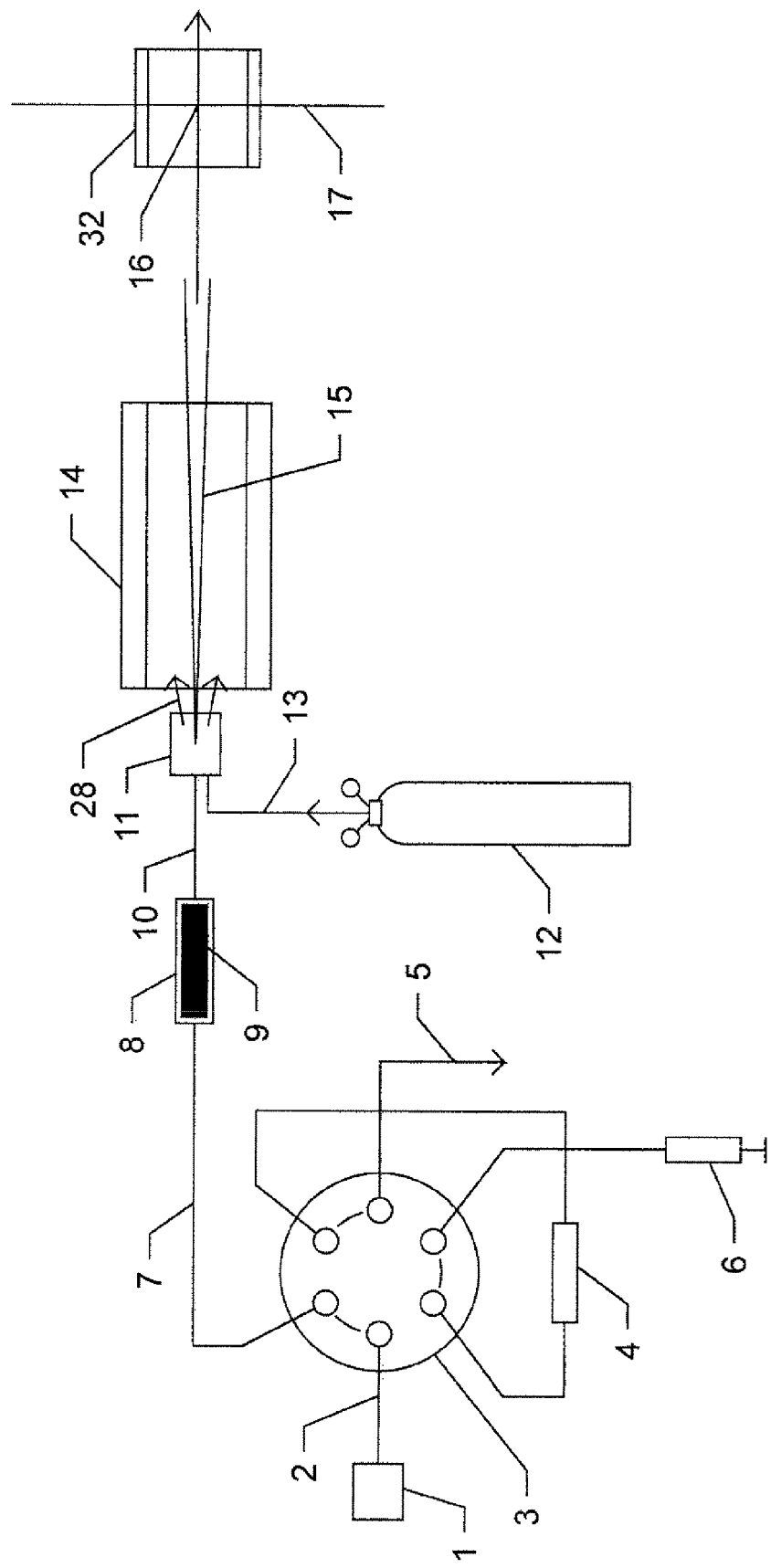
FIG. 1 is a simplified drawing showing part of a chromatographic analyser and analyte detector according to one embodiment of the invention.
Figure 2:
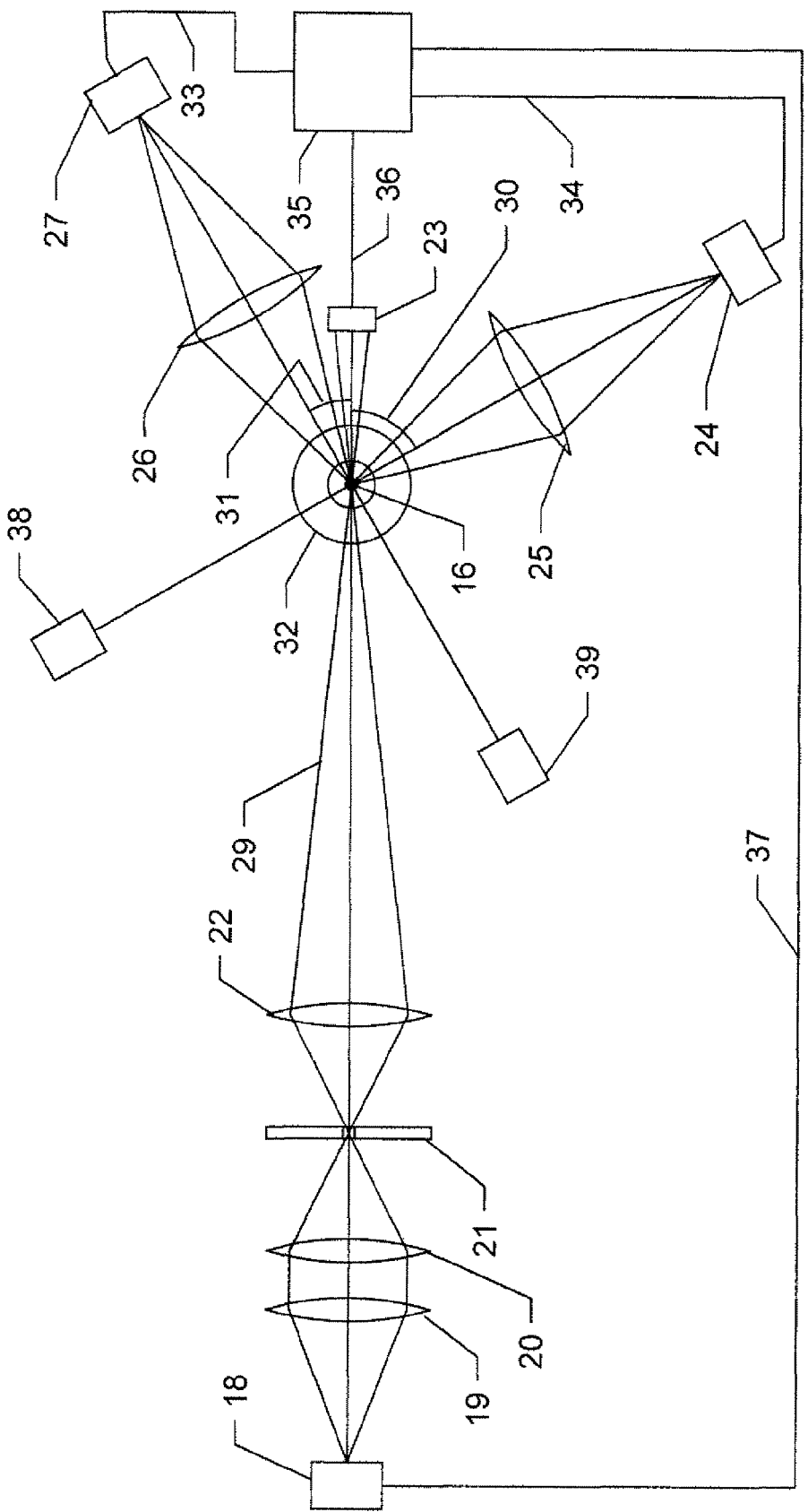
FIG. 2 is a drawing of the optical arrangement of one embodiment of the invention that comprises one beam of radiation and two radiation detectors.

An embodiment of chromatographic apparatus according to the invention, shown in FIGS. 1 and 2, comprises a fluid pump 1 for delivering a flow of a mobile phase, a six-port sample valve 3, a chromatographic column 8 comprising chromatographic separation media 9 and an evaporative light scattering detector comprising items 11 and 14 of FIG. 1, items 18-27 and 33-39 of FIG. 2. The optical system of the evaporative light scattering detector is described in more detail below. The apparatus of FIG. 1 may comprise a liquid chromatograph or high pressure liquid chromatograph, in which case the fluid pump 1 may be capable of delivering a flow of a liquid mobile phase through a pipe 2, the sample valve 3, a sample loop 4 and a pipe 7 to the chromatographic column 8. Alternatively, the FIG. 1 apparatus may comprise a supercritical fluid chromatograph in which the fluid pump 1 is arranged to deliver a flow of a supercritical fluid under pressure (for example, liquid carbon dioxide).

Analytes may be introduced into the fluid flow in pipe 7 by setting valve 3 so that analytes present in a sample injector 6 may flow through the sample loop 4 and to waste via a pipe 5, so that the sample loop 4 is charged with analytes. Valve 3 may then be set so that the fluid from the pump 3 passes through the loop 4 and causes the analytes to be carried through pipe 7 to the column 8.

The chromatographic separation media 9 comprised in the column 8 may be any suitable type. For example, it may be adapted for normal- or reverse-phase chromatography, size-exclusion chromatography, affinity chromatography, ion-exchange chromatography or supercritical fluid chromatography, or combinations of these. The mobile phase supplied by the fluid pump 1 may be selected to be suitable for the separation to be carried out on the chosen chromatographic separation media 9. Analytes may be retained on the separation media 9 for different periods of time so that a flow of fluid leaving the column 8 in a pipe 10 may comprise a flow of mobile phase in which analytes appear sequentially as chromatographic peaks.

It will be appreciated that the apparatus described above is similar to a simple type of prior chromatographic apparatus and that items 1-10 may be replaced by alternative chromatographic systems without departing from the spirit of the invention. Such alternative systems may comprise gradient elution pumping systems and/or multi-dimensional chromatographic systems employing two or more chromatographic columns and associated flow switching valves.

In the FIG. 1 embodiment, analytes present in the fluid flow in pipe 10 may be passed to a nebulizer 11 that generates an aerosol 28. The nebulizer 11 may be a pneumatic nebulizer supplied with a flow of an inert gas (typically nitrogen or argon) through a pipe 13 from a reservoir or pressurized cylinder 12. Such nebulizers are well known and need not be described in detail. A suitable type is a concentric flow nebulizer in which the fluid to be nebulized is caused to flow in a capillary tube and the inert gas flowing through the pipe 13 is introduced into a larger bore tube disposed around the capillary tube. In such a nebulizer a jet of liquid is expelled from the capillary tube and is broken up into droplets through interaction with the gas leaving the larger bore tube, thereby creating the aerosol 28. Other types of nebulizer, for example a cross-flow nebulizer or a mechanical nebulizer such as a piezoelectric nebulizer may also be employed.

The aerosol 28 enters a drift chamber 14 that may comprise a long tubular member (in some embodiments, up to 1 m long), the walls of which may be heated. A long drift chamber may be formed into a coil for convenience. Other suitable types of drift chamber, for example a glass cylinder, may also be used. The temperature of the walls of the chamber may be controlled by a temperature sensor controller (not shown). Solvent is evaporated from the droplets comprised in the aerosol 28 as they pass through the drift chamber so that analytes present in the droplets emerge from it in the form of a stream of particles 15. These particles may comprise small solid particles of an analyte, small droplets comprising analyte, or solvated analyte species. Analytes present in the stream of particles 15 pass into a scattering chamber 32 and may then be detected by means of the optical system shown in FIG. 2. The optical system of FIG. 2 may be disposed in a plane 17 orthogonal to the direction of the travel of the particles such that the particles travel through an area around point 16 in the plane 17.

In the case of apparatus for supercritical fluid chromatography, the nebulizer 11 may be replaced by a pressure reducer through which the fluid expands to generate a gas comprising particles of analyte (when present). The fall in temperature during the expansion may be minimized by heating the pressure reducer. The pressure reduction-drift chamber system so provided may produce a stream of particles 15 that pass into the scattering chamber 32 and through the plane 17 through an area around the point 16.

Referring next to FIG. 2, an embodiment of an optical detection system suitable for use in the chromatographic apparatus comprises a source of radiation 18 and first and second radiation detectors 24 and 27. Conveniently, the source of radiation 18 comprises a filament lamp producing visible light and the detectors 24 and 27 are photomultipliers that respond to visible light. However, other radiation sources and detectors, operable at different frequencies, may alternatively be provided, as discussed in general terms above. Light from the radiation source 18 is focused in a first radiation beam 29 on to an area around the point 16 (through which the stream of particles 15 passes in the scattering chamber 32) by two condenser lenses 19, 20 and a beam-focusing lens 22. An aperture 21 (in this embodiment comprising a slit, but other shapes such as a circular aperture may be used) limits the size of the first radiation beam 29 at the point 16. When particles are present in the vicinity of point 16, radiation is scattered from the first radiation beam 29 and at least some is received by the first and second collection lenses 25 and 26. Lenses 25 and 26 and detectors 24 and 27 are disposed so that the first radiation detector 24 receives radiation scattered at a first angle 30 to the beam 29 and radiation detector 27 receives radiation scattered at a second angle 31 to the beam 29. In this particular embodiment, the first angle 30 may be approximately 75° and the second angle 31 may be approximately 20°, but other angles may also be used. Typically, the lenses and detectors may be such that each detector receives radiation scattered within about ±5° of the first or second angle. Signals from the detectors 24 and 27 are received via connections 34 and 33, respectively, by a control and display system 35 which may comprise a computer or other digital signal processing apparatus. The display and control system 35 may generate an output signal indicative of the presence and/or quantity of particles causing the scattered radiation. It may conveniently be part of a more comprehensive control system that also controls the nebulizer and drift chamber of FIG. 1, and preferably an entire chromatographic apparatus also incorporating the sample valve system and chromatographic column also shown in FIG. 1.

A beam detector 23 disposed on the axis of the radiation beam 29 and is connected to the control and display system 35 by connection 36. Typically, the beam detector 23 may comprise a photodiode. It receives radiation that has passed through the scattering chamber 32 without being scattered, and the signal it generates may be used by the control and display system 35 to monitor or to monitor and control the power to the radiation source 18 via connection 37 in order to maintain constant the intensity of beam 29. Alternatively, the signal from the beam detector 23 may be used to correct the output signal generated by the display and control system 35 for variations in the intensity of the radiation beam 29.

In order to reduce background radiation in the scattering chamber 32, radiation traps 38 and 39 may be provided opposite the detectors 24 and 27. Each trap may conveniently comprise a Rayleigh horn.

Figure 3:
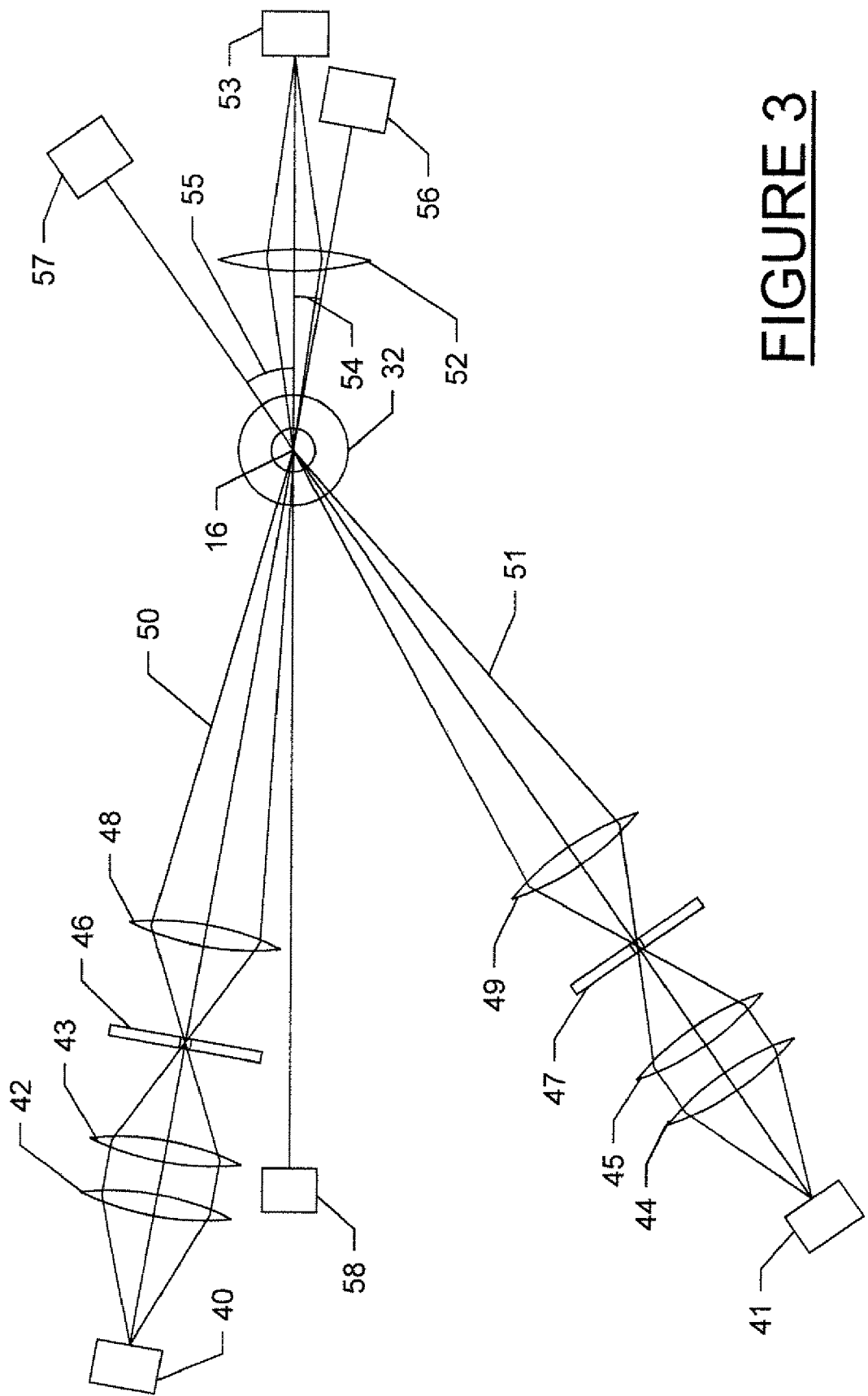
FIG. 3 is a drawing of the optical arrangement of another embodiment of the invention that comprises two beams of radiation and one radiation detector.

In the embodiment shown in FIG. 3, means for generating first and second beams 50, 51 of radiation comprise two radiation sources 40, 41, condenser lenses 42-45, slits or apertures 46 and 47 and beam-focusing lenses 48 and 49. These components are similar to components 18-22 shown in FIG. 2 and are arranged to focus the two beams of radiation 50 and 51 onto an area around the point 16 in the scattering chamber 32. As in the FIG. 2 embodiment, a stream of particles may pass through the point 16 when analytes are present and scatter radiation from either or both of the radiation beams 50, 51 towards a collection lens 52 and then to a radiation detector 53. The radiation detector 53 and lens 52 are disposed so that they receive radiation scattered at a first angle 54 from the first radiation beam 50 and at a second angle 55 from the second radiation beam 51. Beam detectors 56 and 57 are disposed as shown to receive unscattered radiation from beams 50 and 51 respectively. Signals from these beam detectors may be used to monitor or control the intensity of the radiation emitted by the sources 40 and 41 respectively, or to correct the output signal from the display and control means 35, as in the case of the similar system shown in FIG. 2 in respect of the beam 29 and detector 23. A light trap 58 may be provided opposite to the radiation detector 53 to reduce background radiation in the scattering chamber 32.

Figure 4:
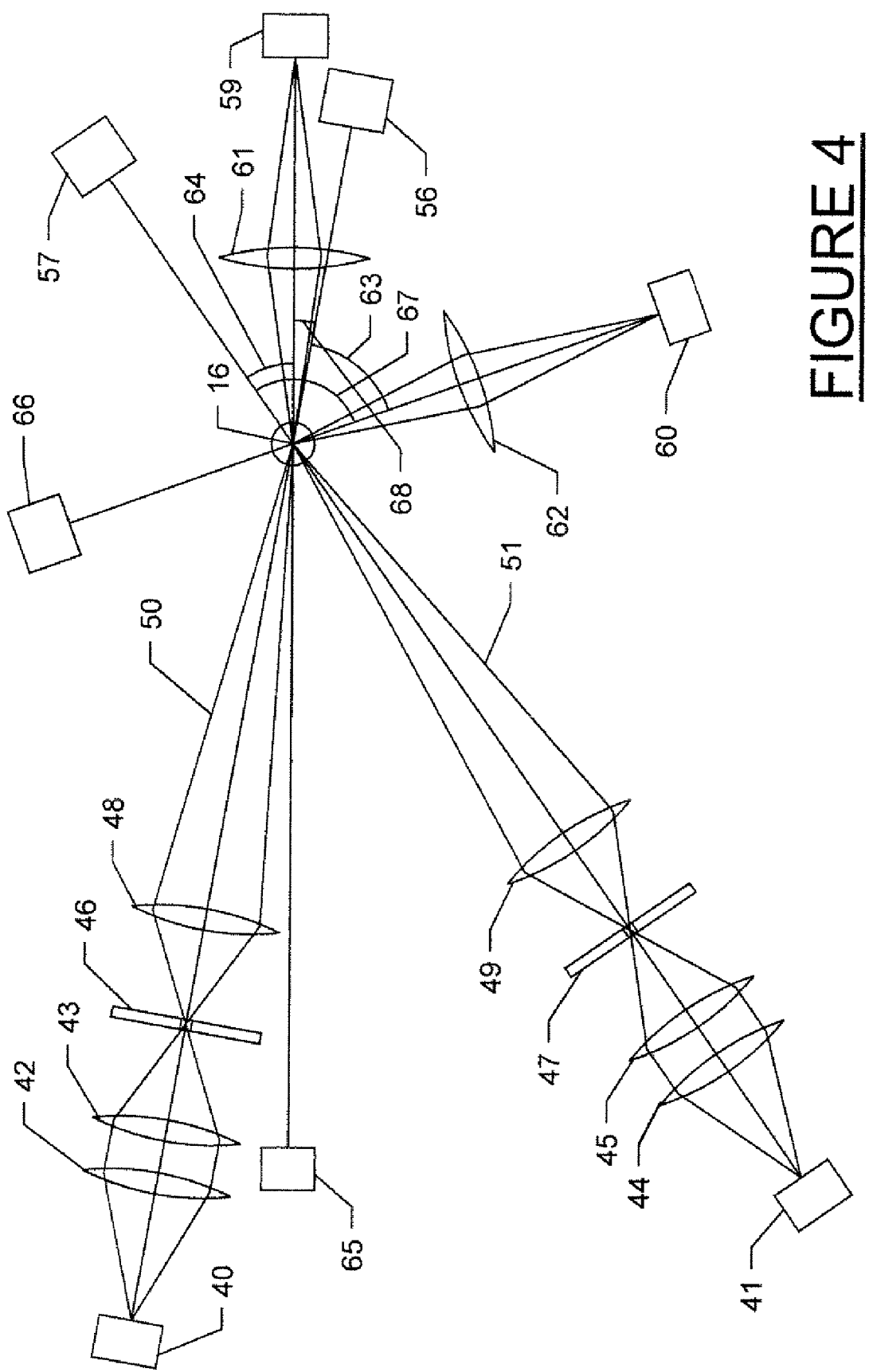
FIG. 4 is a drawing of the optical arrangement of another embodiment of the invention that comprises two beams of radiation and two radiation detectors.

Another embodiment is shown in FIG. 4. In this embodiment, two beams of radiation 50, 51 are provided by means of the radiation source and lens systems comprising items 40-49, as in the case of the FIG. 3 embodiment. Beam detectors 56 and 57 are also provided to allow a control and display system (not shown) to monitor or maintain constant the intensity of the beams, or to correct the output signal of the display and control means 35, as described previously. Two radiation detectors 59 and 60 and their associated beam focusing lenses 61 and 62 are also provided. These are disposed so that lens 62 and detector 60 receive radiation scattered at a first angle 63 to a first radiation beam 50 and so that lens 61 and detector 59 receive radiation scattered at a second angle 64 to the second radiation beam 51. The first angle 63 differs from the second angle 64. Light traps 65 and 66 are also provided, opposite to the detectors 59 and 60 respectively.

The FIG. 4 embodiment also has the advantage that not only is radiation detected at first ad second angles 63 and 64, but may also be detected at a third angle 67 between the second radiation beam 51 and the first detector system 60 and 62, and at a fourth angle 68 between the first radiation beam 50 and the second detector system 61 and 59.

In all the embodiments described above it will be appreciated that scattered radiation is detected at least at two different angles to a beam or beams of radiation. This can be advantageous in improving the sensitivity and/or signal-to-noise ratio of an ELSD and/or chromatographic apparatus incorporating an ELSD is improved in comparison with prior apparatus in which scattered radiation is detected at only one angle. When more than one radiation detector is provided, the control and display system (eg, 35 in FIG. 2) may be adapted to combine, conveniently by adding, the signals from each detector, but other methods of combining the signals may be used. For example, signals may be selected, or their relative contributions adjusted, according to the anticipated nature or size of the analyte particles, or during the course of analysis according to the expected numbers of particles. Signal-to-noise ratios may also be improved by the use of coincident detection techniques. For example, the signals from two detectors may be correlated in time so that an output is generated only when both detectors simultaneously record the passage of a particle though both radiation beams. Such a technique is particularly useful when associated with a pulse-counting detector control system rather than the analogue amplifier system most commonly employed in prior ELSDs. Further advantage may be obtained by the use of coherent radiation sources (for example, lasers) and using Phase Doppler Anemometry to measure both the size and velocity of the particles, thereby reducing the effect of background radiation scattering.

Figure 5:
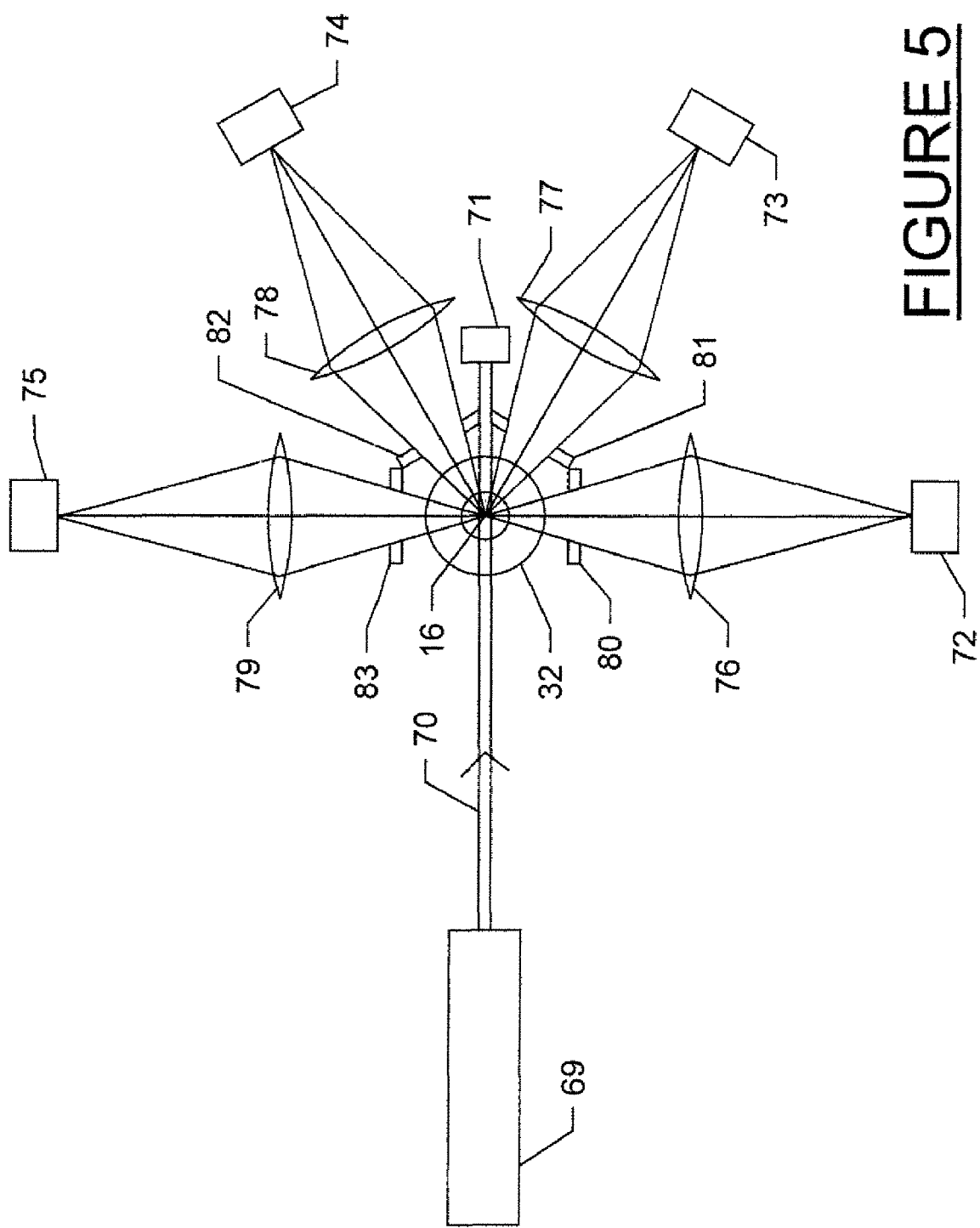
FIG. 5 is a drawing of the optical arrangement of yet another embodiment of the detector that comprises four radiation detectors.

Another embodiment of the invention is shown if FIG. 5. A laser (for example, a 1 mW He/Ne laser) 69 is used to produce a narrow beam of light 70 that passes through the scattering chamber 32 and the point 16 through which passes the stream of particles (FIG. 1). Also provided is a beam detector 71 to receive unscattered light. A signal from the detector 71 may be used to monitor the intensity of the beam 70 and optionally to maintain it substantially constant, as previously described. The beam detector 71 may conveniently comprise a photodiode. Four light sensitive detectors 72-75 and beam focusing lenses 76-79 are provided, disposed around the scattering chamber 32 to receive light scattered by the particles passing through the point 16. Each of the detectors 72-75 may also comprise a photodiode or an array of photodiodes.

The disposition of detectors shown in FIG. 5 is such that detectors receive light scattered at a variety of angles to the beam 70. One or more of the detectors may be positioned to receive light scattered at the same angle as another of he detectors, and while this may be less advantageous than their being positioned to receive light scattered at different angles, it does result in there being detected a greater proportion of he light scattered at one angle. However, provision of a relatively large number of detectors may also increase the detection of background scattered light (see below). This may be minimized by limiting the angular range received by each detector, for example by the aperture defining stops 80-83.

As well as the specific embodiment shown in FIGS. 1-5, it is within the scope of the invention to use any combination of radiation sources and detectors such that the total number of sources and detectors is greater than four. For example, a second laser or other radiation source might replace one of the detectors 74 or 75 in FIG. 5.

Without wishing to be bound by theory, the inventors believe that improved performance may be achieved by apparatus as described due to the nature of light scattering by small particles. For example) the angle at which maximum forward scattering takes place is dependent on the size, shape and composition of the analyte particles. Consequently, detection at only one angle is likely only to result in maximum sensitivity for certain analyte particles. Other analyte particles may fail to be detected, or be detected with reduced sensitivity, because they result in less scattering at that particular angle. Further, it has been observed that the size of the analyte particles varies with the concentration of an analyte in the mobile phase entering the nebulizer. Typically, the particle size increases with increasing analyte concentration, which results in greater scattering at low angles relative to the incident radiation beam. Given that the fixed scattering angle in prior ELSDs is typically selected to result in maximum sensitivity at low analyte concentrations (close to the limit of detection), sensitivity will most likely be lower at higher concentrations at which most particles will be scattered at smaller angles. It is thought that this effect is at least one cause of the characteristic non-linearity of prior ELSDs, which reduces their usefulness for quantitative analyses. Apparatus as described herein, in which scattering at more than one angle may be detected, has been found to result in improved linearity with respect to analyte concentration.

Further, the inventors have recognized that scattering of radiation by the particles is fundamentally different from the scattering caused by the presence of gas molecules in the scattering chamber, which usually results in a significant background signal in prior ELSDs. This background scattering may be described by the Rayleigh theory and results in a relatively constant signal at the radiation detectors(s) providing that the nature and pressure of the gas remain constant. However, in practice, its presence does detract from the detection limits of prior ELSDs because it is relatively large in comparison to the signals due to scattering by the stream of particles and also because in a typical chromatographic separation the nature of the gas in the scattering chamber will change as the mobile phase composition changes. However, because the scattering due to the particles, which are typically physically larger than the gas molecules, is better described by the Mie theory or by refraction/reflection scattering theory, and also because the particles move quickly through the radiation beam (typically they may be present in the beam for about 7 ms), the frequency signature of the signals due to scattering by the analyte particles is quite different from that due to the background gas molecules. Thus the invention may provide data processing techniques and apparatus to enhance the particle scattering signals relative to the background scattering signal generated by one or more of the radiation detectors. These techniques may conveniently comprise digital signal processing implemented either by hardware components or by software comprised in the control and display system 35 used to handle data generated by the radiation detectors themselves. Computers suitable for digital signal processing are available from several vendors including Dell Computer (Houston, Tex., USA) and Apple Computers, Inc. (Cupertino, Calif., USA). The digital signal processing may take any suitable form capable of recognizing the difference in the frequency signatures characteristic of the background Rayleigh scattering and the transient particle scattering, and may be configured to reject signals characteristic of the background scattering. For example, it may be arranged to reject signals that are present for a significantly longer time than the typical transit time of the particles through the radiation beam. The digital filtering may be carried out by the use of a Fourier Transform to transform the signal into the frequency domain, convolution of the transformed signal with a predetermined function characteristic of a particle scattering signal, followed by a transform to return the correlated data to the time domain, but other methods may also be used. Such data enhancement techniques are known in the art and need not be described in detail.

In order to maximize the advantage obtainable from such digital data processing techniques it may be advantageous to provide radiation detectors capable of providing high-bandwidth analogue signals or to provide photon-counting detectors.

Such digital filtering of the signals from an ELSD radiation detector may also be used with ELSDs comprising only a single radiation source and detector.

It will be appreciated that detection at several different scattering angles can be achieved in practice by the provision of multiple detectors and a single source of radiation (for example, the FIG. 2 embodiment), a single detector and multiple sources of radiation (eg, the FIG. 3 embodiment), or by both multiple detectors and multiple sources of radiation (eg, the FIG. 4 embodiment). In cases where more than one source of radiation is provided, the sources may be arranged to have different frequencies (for example, a visible light source and a UV or IR source may be provided). Such a configuration may mitigate another problem of prior ELSDs, namely the failure to detect, or to detect only at a reduced sensitivity, certain analyte particles which strongly absorb, rather than scatter radiation at the frequency of the source.

What is claimed is:

1. Apparatus for the detection of one or more analytes present in a fluid, said apparatus comprising:
   a) vessel means in communication with a source of fluid, and operable to evaporate solvent from said fluid and, in the presence of an analyte, to produce a stream of particles;
   b) a radiation source in photo communication with said vessel means for generating a plurality of beams of radiation within said vessel means, said a plurality of beams of radiation directed to and received by said stream of particles in said vessel means to produce at least one first reflected beam having a first scattering angle and to produce at least one second reflected beam having a second scattering angle; and
   c) radiation detection means in photo-communication with said vessel means for receiving said first reflected beam at said first scattering angle and producing a first scattering angle signal and for receiving said second reflected beam at said second scattering angle and producing a second scattering angle signal; said first scattering angle signal and said second scattering angle signal indicative of the presence or absence or quantity of an analyte.

2. The apparatus of claim 1 further comprising a source of fluid.

3. The apparatus of claim 1 wherein said fluid is selected from the group of fluids consisting of supercritical fluids and liquids.

4. The apparatus of claim 1 wherein said source of fluid is a chromatographic instrument.

5. The apparatus of claim 1 wherein said radiation detection means comprises a first radiation detector and a second radiation detector, said first radiation detector being constructed and arranged to receive reflected radiation at said first scattering angle and said second radiation detector being constructed and arranged to receive reflected radiation at said second scattering angle.

6. The apparatus of claim 5 further comprising signal processing means in signal communication with said radiation detection means for receiving signals from said first and said second radiation detectors and associating signals characteristic of a particle passing through a said radiation beam received by said first radiation detector and said second radiation detectors at substantially the same time.

7. The apparatus of claim 1 wherein said radiation source generates a first beam of radiation and a second beam of radiation, said radiation detection means being disposed to receive radiation reflected at said first scattering angle to said first beam of radiation and at said second scattering angle to said second beam of radiation.

8. The apparatus of claim 7 wherein said radiation detection means comprises a first radiation detector and a second radiation detector, said first radiation detector being disposed to receive radiation scattered by said particles at said first angle to said first beam of radiation and said second radiation detector being disposed to receive radiation scattered by said particles at said second angle to said second beam of radiation.

9. The apparatus of claim 7 wherein said first and said second beams of radiation have different frequencies.

10. The apparatus of claim 7 wherein said radiation beams and said radiation detection means are disposed in a plane substantially orthogonal to said stream of particles.

11. The apparatus of claim 1 wherein said means for generating at least one beam of radiation generates radiation selected from the group comprising:
 a) visible light;
 b) infrared radiation;
 c) ultraviolet radiation.

12. The apparatus of claim 1 wherein said means for generating a plurality of beams of radiation comprises at least one radiation source selected from the group comprising:
 a) filament lamps;
 b) discharge lamps;
 c) arc lamps;
 d) light emitting diodes;
 e) laser diodes;
 f) lasers.

13. The apparatus of claim 1 wherein said radiation detection means comprises at least one radiation detector selected from the group comprising:
 a) photomultipliers;
 b) photodiodes;
 c) phototransistors;
 d) other photosensitive solid state devices;
 e) scintillator devices and associated electron detectors;
 f) thermal detectors;
 g) radiation sensitive film.

14. The apparatus of claim 1 wherein said radiation source generates a first beam of radiation having a first frequency and a second beam of radiation having a second frequency, and wherein said first and second frequencies are different.

15. The apparatus of claim 1 wherein vessel means comprises a nebulizer and a heated drift region.

16. The apparatus of claim 1 wherein said radiation detection means comprises a plurality of radiation detectors.

17. The apparatus of claim 16 wherein said radiation sources and said radiation detectors are disposed so that between them they receive at least radiation scattered at a first angle to a first beam of radiation and at a second angle to the first or a second beam of radiation.

18. The apparatus of claim 17 wherein said first and said second angles are different.

19. The apparatus of claim 18 wherein radiation scattered at both the first and second angles is detected simultaneously.

20. The apparatus of claim 1 wherein radiation scattered at both the first and second angles is detected simultaneously.

21. The apparatus of claim 1 further comprising signal processing means in signal communication with said radiation detection means for receiving said first scattering angle signal and said second scattering angle signal from said radiation detection means.

22. The apparatus of claim 21 wherein at least one of said first light scattering signal and said second light scattering signal has a frequency signature of said particles and said signal processing means comprises means for enhancing signals having said frequency signatures.

23. The apparatus of claim 21 wherein said signal processing means comprises means for rejecting signals present for a time significantly longer than the transit time of said particles through at least one of said beams of radiation.

24. The apparatus of claim 1 wherein said radiation source for generating a plurality of beams of radiation comprises a plurality of radiation sources.

25. The apparatus of claim 1 wherein said a plurality of beams of radiation are generated simultaneously within said vessel means.

26. A method of detecting the presence or absence of one or more analytes in a fluid comprising the steps of
 providing an apparatus having vessel means, a radiation source, and radiation detection means, said vessel means in communication with a source of fluid, and operable to evaporate solvent from said fluid and, in the presence of an analyte, to produce a stream of particles; said radiation source in photo communication with said vessel means for generating a plurality of beams of radiation within said vessel means, said a plurality of beams of radiation directed and received by said stream of particles in said vessel means to produce at least one first reflected beam having a first scattering angle and to produce at least one second reflected beam having a second scattering angle; and said radiation detection means in photo-communication with said vessel means for receiving said first reflected beam at said first scattering angle and producing a first scattering angle signal and for receiving said second reflected beam at said second scattering angle and producing a second scattering angle signal; said first scattering angle signal and said second scattering angle signal indicative of the presence or absence or quantity of an analyte;
 placing a fluid in said vessel means and forming a stream of particles, and generating a plurality of beams of radiation directed at said stream of particles and receiving at least one reflected beam having a first scattering angle or a second scattering angle indicative of the presence or absence or quantity of an analyte.

27. The method of claim 26 wherein said source of fluid is a chromatographic instrument.

28. The method of claim 26 wherein said radiation detection means comprises a first radiation detector and a second radiation detector, said first radiation detector being constructed and arranged to receive reflected radiation at said first scattering angle and said second radiation detector being constructed and arranged to receive reflected radiation at said second scattering angle.

29. The method of claim 26 wherein said radiation source generates a first beam of radiation and a second beam of radiation, said radiation detection means being disposed to receive radiation reflected at said first scattering angle to said first beam of radiation and at said second scattering angle to said second beam of radiation.

30. The method of claim 29 wherein said radiation detection means comprises a first radiation detector and a second radiation detector, said first radiation detector being disposed to receive radiation scattered by said particles at said first angle to said first beam of radiation and said second radiation detector being disposed to receive radiation scattered by said particles at said second angle to said second beam of radiation.

31. The method of claim 26 wherein said radiation source generates a first beam of radiation having a first frequency and a second beam of radiation having a second frequency, and wherein said first and second frequencies are different.

32. The method of claim 31 wherein said radiation sources and said radiation detectors are disposed so that between them they receive at least radiation scattered at a first angle to a first beam of radiation and at a second angle to the first or a second beam of radiation.

33. The method of claim 26 wherein radiation scattered at both the first and second angles is detected simultaneously.

34. The method of claim 26 wherein at least one of said first light scattering signal and said second light scattering signal has a frequency signature of said particles and said method comprises the step of enhancing signals having said frequency signatures.

35. The method of claim 26 comprises the step of rejecting signals present for a time significantly longer than the transit time of said particles through at least one of said beams of radiation.

36. The method of claim 26 further comprising the step of receiving signals from said first and said second radiation detectors and associating signals characteristic of a particle passing through a said radiation beam received by said first radiation detector and said second radiation detectors at substantially the same time.

37. The method of claim 26 wherein said radiation detection means comprises a plurality of radiation detectors.

38. The method of claim 26 wherein said radiation source for generating a plurality of beams of radiation comprises a plurality of radiation sources.

39. The method of claim 26 wherein said a plurality of beams of radiation are generated simultaneously within said vessel means.

40. A method of detecting the presence of one or more analytes in a fluid, said method comprising evaporating solvent from said fluid to produce a stream of particles whenever a said analyte is present in said fluid, passing said stream of particles through multiple beams of radiation generated from a plurality of radiation sources so that at least some of said particles scatter radiation therefrom, and detecting both radiation scattered at a first angle to a said beam of radiation and at a second, different, angle to a said beam of radiation.

41. A method as claimed in claim 40 for the detection of analytes in the eluant from liquid or supercritical fluid chromatographic separation media.

42. A method as claimed in claim 40 wherein said beams of radiation are selected from the group comprising:
a) visible light;
b) ultraviolet radiation;
c) infrared radiation.

43. A method as claimed in claim 40 further comprising separately detecting radiation scattered by said particles at a first angle and at a second, different, angle to a beam of radiation.

44. A method as claimed in claim 40 further comprising detecting radiation scattered by the particles at a first angle to a first beam of radiation and at a second, different, angle to a second beam of radiation.

* * * * *